US011684446B2

(12) United States Patent
Adler, Jr. et al.

(10) Patent No.: US 11,684,446 B2
(45) Date of Patent: Jun. 27, 2023

(54) DEVICE FOR RADIOSURGICAL TREATMENT OF UTERINE FIBROIDS

(71) Applicant: Zap Surgical Systems, Inc., San Carlos, CA (US)

(72) Inventors: John R. Adler, Jr., Stanford, CA (US); M. Bret Schneider, Sunnyvale, CA (US)

(73) Assignee: Zap Surgical Systems, Inc., San Carlos, CA (US)

(*) Notice: Subject to any disclaimer, the term of this patent is extended or adjusted under 35 U.S.C. 154(b) by 443 days.

(21) Appl. No.: 16/787,234

(22) Filed: Feb. 11, 2020

(65) Prior Publication Data

US 2020/0268475 A1    Aug. 27, 2020

Related U.S. Application Data

(60) Provisional application No. 62/811,402, filed on Feb. 27, 2019.

(51) Int. Cl.
*A61B 90/00* (2016.01)

(52) U.S. Cl.
CPC ...... *A61B 90/39* (2016.02); *A61B 2090/3912* (2016.02); *A61B 2090/3983* (2016.02); *A61B 2090/3987* (2016.02)

(58) Field of Classification Search
CPC .................................. A61B 90/39; A61F 6/00
See application file for complete search history.

(56) References Cited

U.S. PATENT DOCUMENTS

| 2,595,260 A | 5/1952 | Hollstein |
| 2,781,454 A | 2/1957 | Green et al. |

(Continued)

FOREIGN PATENT DOCUMENTS

| CN | 2533895 | 2/2003 |
| DE | 3321057 | 12/1984 |

(Continued)

OTHER PUBLICATIONS

Bodduluri et al., "X-ray guided robotic radiosurgery for solid tumors", Industrial Robot: An International Journal, vol. 29, No. 3, 2002, pp. 221-227.

(Continued)

*Primary Examiner* — Angela M Hoffa
*Assistant Examiner* — Younhee Choi
(74) *Attorney, Agent, or Firm* — Kilpatrick Townsend & Stockton LLP (57) ABSTRACT

Removable marker implants having fiducial markers disposed on multiple elongate members extend and splay laterally outward when deployed thereby providing improved 3D localization and tracking of a portion of the patient's body for stereotactic radiosurgery. Such an approach is particularly useful for tracking of the uterus during radiosurgery treatment of uterine fibroids. Such implants can include an outer sheath that contains the multiple elongate members during delivery into the portion of the body. The elongate members can be slidably disposed within the shaft and advanced into an expanded deployed position by advancement of an applicator shaft or rod within the sheath. Marker implant can also be integrally formed implants with flexible arms having fiducial markers thereon that can be constrained in a sheath for delivery and resiliently splay laterally outward when released from the shaft. Methods of delivery and deployment are also provided.

24 Claims, 8 Drawing Sheets

(56) References Cited

U.S. PATENT DOCUMENTS

| | | | |
|---|---|---|---|
| 2,818,510 A | 12/1957 | Hansheinrich |
| 2,890,349 A | 6/1959 | Laszlo |
| 3,082,322 A | 3/1963 | Koerner et al. |
| 3,281,598 A | 10/1966 | Irene |
| 3,349,242 A | 10/1967 | Braestrup |
| 3,466,439 A | 9/1969 | Setala |
| 3,488,495 A | 1/1970 | Schneeman |
| 3,588,499 A | 6/1971 | Pegrum |
| 3,617,749 A | 11/1971 | Massiot |
| 3,670,163 A | 6/1972 | Lajus |
| 3,803,418 A | 4/1974 | Holstrom |
| 3,833,813 A | 9/1974 | James |
| 3,868,506 A | 2/1975 | Ogiso |
| 3,892,967 A | 7/1975 | Howarth et al. |
| 4,139,775 A | 2/1979 | Williams |
| 4,177,382 A | 12/1979 | Hounsfield |
| 4,209,706 A | 6/1980 | Nunan |
| 4,266,135 A | 5/1981 | Kuwik et al. |
| 4,288,700 A | 9/1981 | Grass et al. |
| 4,339,825 A | 7/1982 | Barrett et al. |
| 4,358,856 A | 11/1982 | Stivender et al. |
| 4,363,128 A | 12/1982 | Grady et al. |
| 4,481,656 A | 11/1984 | Janssen et al. |
| 4,541,108 A | 9/1985 | Grady et al. |
| 4,649,560 A | 3/1987 | Grady et al. |
| 4,653,083 A | 3/1987 | Rossi |
| 4,741,015 A | 4/1988 | Charrier |
| 4,741,105 A | 5/1988 | Wong |
| 4,756,016 A | 7/1988 | Grady et al. |
| 4,866,751 A | 9/1989 | Louiday |
| 4,922,512 A | 5/1990 | Lajus et al. |
| 4,977,585 A | 12/1990 | Boyd |
| 4,987,585 A | 1/1991 | Kidd et al. |
| 4,998,268 A | 3/1991 | Winter |
| 5,038,371 A | 8/1991 | Janssen et al. |
| 5,040,203 A | 8/1991 | Janssen et al. |
| 5,048,069 A | 9/1991 | Siczek |
| 5,048,071 A | 9/1991 | Van |
| 5,052,036 A | 9/1991 | Grady |
| 5,073,917 A | 12/1991 | Van et al. |
| 5,086,447 A | 2/1992 | Siczek et al. |
| 5,095,501 A | 3/1992 | Kobayashi |
| 5,155,757 A | 10/1992 | Sakaniwa et al. |
| 5,159,622 A | 10/1992 | Sakaniwa et al. |
| 5,207,223 A | 5/1993 | Adler et al. |
| 5,379,333 A | 1/1995 | Toth |
| 5,420,427 A | 5/1995 | Morgan et al. |
| 5,537,452 A | 7/1996 | Shepherd et al. |
| 5,577,094 A | 11/1996 | Fudamoto |
| 5,634,929 A | 6/1997 | Misko et al. |
| 5,699,446 A | 12/1997 | Rougee et al. |
| 5,751,781 A | 5/1998 | Brown et al. |
| 5,835,557 A | 11/1998 | Malmstroem |
| 5,945,684 A | 8/1999 | Lam et al. |
| 6,104,779 A | 8/2000 | Shepherd et al. |
| 6,155,713 A | 12/2000 | Watanabe |
| 6,198,957 B1 | 3/2001 | Green |
| 6,217,214 B1 | 4/2001 | Cabral et al. |
| 6,309,102 B1 | 10/2001 | Stenfors |
| 6,325,538 B1 | 12/2001 | Heesch |
| 6,614,871 B1 | 9/2003 | Kobiki et al. |
| 6,789,941 B1 | 9/2004 | Grady |
| 6,856,670 B2 | 2/2005 | Hoheisel |
| 6,888,919 B2 | 5/2005 | Graf |
| 6,969,194 B1 | 11/2005 | Naefstadius |
| 7,188,999 B2 | 3/2007 | Mihara et al. |
| 7,295,648 B2 | 11/2007 | Brown |
| 7,302,038 B2 | 11/2007 | Mackie et al. |
| 7,526,066 B2 | 4/2009 | Koshnitsky et al. |
| 7,649,981 B2 | 1/2010 | Seppi et al. |
| 8,139,714 B1 | 3/2012 | Sahadevan |
| 8,406,844 B2 | 3/2013 | Ruchala et al. |
| 8,500,760 B2* | 8/2013 | McLawhorn ........ A61B 17/068 |
| | | 606/151 |
| 8,913,716 B2 | 12/2014 | Sobering et al. |
| 9,014,341 B2 | 4/2015 | Zhang et al. |
| 9,208,918 B2 | 12/2015 | Tybinkowski et al. |
| 9,308,395 B2 | 4/2016 | Adler, Jr. et al. |
| 9,314,160 B2 | 4/2016 | Adler, Jr. et al. |
| 9,604,077 B2 | 3/2017 | Xing et al. |
| 9,757,593 B2 | 9/2017 | Adler et al. |
| 10,499,861 B2 | 12/2019 | Achkire et al. |
| 2004/0170254 A1 | 9/2004 | Gregerson et al. |
| 2004/0251419 A1 | 12/2004 | Nelson et al. |
| 2005/0049477 A1 | 3/2005 | Fu et al. |
| 2005/0197564 A1 | 9/2005 | Dempsey |
| 2005/0236588 A1 | 10/2005 | Ein-Gal |
| 2007/0189591 A1 | 8/2007 | Lu et al. |
| 2008/0002809 A1 | 1/2008 | Bodduluri |
| 2008/0144908 A1 | 6/2008 | West et al. |
| 2008/0249534 A1* | 10/2008 | Gruber ............. A61B 17/12099 |
| | | 606/198 |
| 2009/0110146 A1 | 4/2009 | Sliski et al. |
| 2009/0163799 A1 | 6/2009 | Erbel et al. |
| 2009/0180678 A1 | 7/2009 | Kuduvalli et al. |
| 2010/0002829 A1 | 1/2010 | Dafni |
| 2010/0183196 A1 | 7/2010 | Fu et al. |
| 2010/0237259 A1 | 9/2010 | Wang |
| 2010/0239066 A1 | 9/2010 | Conolly et al. |
| 2010/0268074 A1 | 10/2010 | Van Loef et al. |
| 2010/0300452 A1* | 12/2010 | Tal ........................... H04R 5/02 |
| | | 128/839 |
| 2011/0210261 A1 | 9/2011 | Maurer |
| 2013/0114872 A1 | 5/2013 | Chen et al. |
| 2013/0136239 A1 | 5/2013 | Laws et al. |
| 2013/0188856 A1 | 7/2013 | Adler, Jr. et al. |
| 2013/0261430 A1 | 10/2013 | Uhlemann |
| 2014/0048074 A1* | 2/2014 | Tai ........................... A61F 6/142 |
| | | 128/833 |
| 2016/0095558 A1 | 4/2016 | Choy et al. |
| 2016/0220848 A1 | 8/2016 | Adler, Jr. et al. |
| 2018/0318607 A1 | 11/2018 | Wilbur et al. |
| 2021/0298942 A1* | 9/2021 | Jutila ..................... A61F 6/142 |

FOREIGN PATENT DOCUMENTS

| | | |
|---|---|---|
| DE | 19728788 | 1/1999 |
| EP | 1075855 | 2/2001 |
| FR | 1587608 | 3/1970 |
| GB | 1129653 | 10/1968 |
| JP | 2885304 | 12/1993 |
| JP | H07255867 | 10/1995 |
| JP | H07265445 | 10/1995 |
| JP | 2000271109 | 10/2000 |
| JP | 2001137372 | 5/2001 |
| JP | 2003024459 | 1/2003 |
| JP | 2003205042 | 7/2003 |
| JP | 2004097646 | 4/2004 |
| JP | 2007148276 | 6/2007 |
| WO | 0074779 | 12/2000 |
| WO | 0112262 | 2/2001 |
| WO | 03018131 | 3/2003 |
| WO | 2003077763 | 9/2003 |
| WO | 2013180883 | 12/2013 |
| WO | 2017100611 | 6/2017 |
| WO | 2018/203918 | 11/2018 |

OTHER PUBLICATIONS

Dong et al., "An Image Correlation Procedure for Digitally Reconstructed Radiographs and Electronic Portal Images", Int. J. Radiation Oncology Biol. Phys., vol. 33, No. 5, 1995, pp. 1053-1060.

Eifel et al., "Gynecologic Radiation Oncology: A Practical Guide", 2016, 1 pg.

Harris et al., "Assessment of Organ Motion in Postoperative Endometrial and Cervical Cancer Patients Treated With Intensity-Modulated Radation Therapy", Int J Radiat Oncol Biol Phys. vol. 81, No. 4, 2011, pp. e645-e650.

Heijkoop et al., "Clinical implementation of an online adaptive plan-of-the-day protocol for nonrigid motion management in locally advanced cervical cancer IMRT", International Journal of Radiation Oncology Biology Physics vol. 90, No. 3, 2014, pp. 673-679.

(56) References Cited

OTHER PUBLICATIONS

Hissoiny et al., "GPUMCD: a new GPU-Oriented Monte Carlo dose calculation platform", physics.med-ph, Jan. 2011, 28 pp.
Jonsson et al., "Internal Fiducial Markers and Susceptibility Effects in MRI-Simulation and Measurement of Spatial Accuracy", Int J Radiat Oncol Biol Phys. vol. 82, No. 5, 2012, pp. 1612-1618.
Jung et al., "Flexible Gd2O2S:Tb scintillators pixelated with polyethylene microstructures for digital x-ray image sensors", J. Micromech. Microeng. 19, 2009, 10pp.
Kaatee et al., "Detection of Organ Movement in Cervix Cancer Patients Using a Fluoroscopic Electronic Portal Imaging Device and Radiopaque Markers", Int. J. Radiat. Oncol. Biol. Phys. vol. 54, No. 2, 2002, pp. 576-583.
Latifi et al., "Assessment of intact cervix motion using implanted fiducials in patients treated with helical tomotherapy with daily MVCT positioning", J Radiat Oncol 2, 2013, pp. 323-329.
Li et al., "Interfractional Variations in Patient Setup and Anatomic", Int. J. Radiat. Oncol. Biol. Phys. vol. 68, No. 2, 2007, pp. 581-591.
Lo et al., "Hardware acceleration of a Monte Carlo simulation for photodynamic treatment planning", Journal of Biomedical Optics, vol. 14(1), Jan./Feb. 2009, pp. 014019-1 thru 014019-11.
MacKie et al., "Tomotherapy: a new concept for the delivery of dynamic conformal radiotherapy ", Medical Physics 20, 1709 (1993); doi: 10.1118/1.596958, Jun. 4, 1998, 1709-1719.
Osher et al., "Fast Linearized Bregman Iteration for Compressive Sensing and Sparse Denoising", 2008, pp. 1-19.
Ruchala et al., "Megavoltage CT image reconstruction during tomotherapy treatments", Phys. Med. Biol. vol. 45, 2000, pp. 3545-3562.
Schonberg , "The History of the Portable Linear Accelerator", American Association for Physicists in Medicine, downloaded from the internet: https://www.aapm.org/meetings/2001AM/pdf/7221-68900.pdf, 2001, pp. 1-14.
Weidlich et al., "Characterization of a Novel Revolving Radiation Collimator", Cureus, vol. 10, No. 2, Feb. 2018, pp. 1-9.
Zaman et al., "Scintillating Balloon-Enabled Fiber-Optic System for Radionuclide Imaging of Atherosclerotic Plaques", J Nucl Med 56(5), 2015, 771-777.

\* cited by examiner

DEVICE FOR RADIOSURGICAL TREATMENT OF UTERINE FIBROIDS

CROSS-REFERENCES TO RELATED APPLICATIONS

The present application is a Non-Provisional of and claims the benefit of priority of U.S. Provisional Appln. No. 62/811,402 filed Feb. 27, 2019; the full disclosure which is incorporated herein by reference in its entirety.

This application is generally related to U.S. application Ser. No. 16/123,834 filed Sep. 6, 2018 (now U.S. Pat. No. 10,499,861), entitled "Self-Shielded, Integrated-Control Radiosurgery System;" the entirety of which is incorporated herein by reference for all purposes.

BACKGROUND OF THE INVENTION

Uterine fibroids (also called leiomyomas) are non-cancerous tumors composed of muscle cells, and which frequently grow in the wall of the uterus. Fibroids may be located in the middle of the uterine wall, or may be closer to the internal surface that borders the endometrium, or closer to the external surface within the peritoneal cavity. Fibroids may cause symptoms including lower abdominal or lower back pain, heavy menstrual bleeding, a feeling of fullness in the pelvic area, enlargement of the lower abdomen, frequent urination, pain during sex, complications during pregnancy and labor, and sometimes infertility. Treatments for fibroids include medications including gonadotropin releasing hormone agonists and progesterone analogs, including those eluted by intrauterine devices such as the MIRENA® (Bayer HealthCare Pharmaceuticals Inc., Whippany, N.J. USA). Surgical treatments for uterine fibroids include hysterectomy, electrical or cryogenic myolysis, surgical morcellation and extraction. When reduction of menstrual bleeding is the primary goal, endometrial ablation is an effective treatment option.

Stereotactic radiosurgery is a medical therapy in which beams of high-intensity ionizing radiation (such as x-ray, gamma radiation or proton beam) are directed at one or more targets within the body from a variety of trajectories that all intersect at the target. Because of the intersection of the beams at the target, radiation dose accumulated at that spot becomes high, while that received at other areas along each beam's trajectory remains low. Stereotactic radiosurgery or other forms of external beam radiation therapy are sometimes used for destroying cancer in the uterus or pelvis. When this is done, it is customary to place fiducial markers into the uterus, cervix or other pelvic structures in order to make aim at the target more precise.

These conventional approaches can be further understood by referring to the following references: Eifel and Klopp, "Gynecologic Radiation Oncology: A Practical Guide" 2016; Kaatee et al., "Detection of organ movement in cervix cancer patients using a fluoroscopic electronic portal imaging device and radiopaque markers" *Int J Radiat Oncol Biol Phys.* 54(2):576-83, 2002; Li X A et al., "Interfractional variations in patient setup and anatomic change assessed by daily computed tomography" *Int. J. Radiat. Oncol. Biol. Phys.* Vol. 68, No. 2, pp. 581-91, June 2007; Jonsson et al. "Internal fiducial markers and susceptibility effects in MRI-simulation and measurement of spatial accuracy" *Int J Radiat Oncol Biol Phys.* 82(5):1612-8, April 2011; Harris et al. "Assessment of organ motion in postoperative endometrial and cervical cancer patients treated with intensity-modulated radiation therapy," *Int J Radiat Oncol Biol Phys.* 81(4), 2011; Heijkoop et al. "Clinical implementation of an online adaptive plan-of-the-day protocol for nonrigid motion management in locally advanced cervical cancer IMRT" *Int J Radiat Oncol Biol Phys.* 90(3):673-9, 2014 Nov. 1; Latifi et al. "Assessment of intact cervix motion using implanted fiducials in patients treated with helical tomotherapy with daily MVCT positioning" *J Radiat Oncol*, Vol. 2, Issue 3, pp. 323-329, September 2013. The entireties of which are incorporated herein by reference for all purposes.

Focused ultrasound is another modality in which precise localization of a target is desirable and could benefit from incorporation of the present invention. In focused ultrasound, sonic pulses are used for precision stimulation or heating of targeted tissue deep within the body. One common use of focused ultrasound is to destroy cancerous or otherwise dysfunctional cells or tissue.

Fiducial markers are objects for which their position can be firmly ascertained by some detection modality. Fiducial markers are typically used in order to perform high-precision tracking of the spatial position of another object that may not be readily visible or otherwise not accurately assessable as to location, position or shape. For purposes of precise localization, an array of at least three fiducial markers in different locations in the target (or adjacent) tissue is usually used, generally placed as far apart as possible within the object that needs to be tracked. Fiducial markers known in the art include CT and (KV) X-ray-visible fiducial markers, for example, Gold Soft Tissue Marker (CIVCO Radiotherapy, Orange City, Iowa, USA), GOLD ANCHOR™ (Naslund Medical AB, Sweden), or fiducial markers that may be screwed into targeted tissue, for example, 1.5 mm titanium self-tapping screws (KLS Martin L.P., Jacksonville, Fla., USA). Fiducial markers as previously described do appear in MRI images as areas of signal drop-out, but better MRI-visible fiducial markers like Vitamin E capsules, or VISICOIL MR fiducial markers (IBA, Louvain-La-Neuve, Belgium) are known in the art. Other types of fiducial markers include active signal-emitting devices (e.g., radiofrequency emitting beacons) like the Calypso System (Varian Medical Systems, Palo Alto, Calif.). Still other fiducial markers include infrared-reflecting systems, for example, those by Surgical Navigation Technologies (Broomfield, Colo., USA, a Division of Medtronic, Inc.), Synchrony (Accuray Inc., Sunnyvale Calif., USA). Other fiducial markers include those detectable with visible light such as fiducial arrays (Northern Digital Inc. Waterloo, Ontario, Canada). Conventional approaches of using fiducial markers present challenges when treating an organ or portion of the patient's body that is prone to movement. Placement of individual fiducial markers about an interior of a body cavity or at different locations of the organ can be tedious and difficult to access since the markers must be placed at various anatomical locations, preferably distant from one another. Further, some portions of the body cavity and organs may have surfaces or walls that move relative each other such that the location of a particular marker may not accurately represent the position or movement of the entire organ. Another problem is that implantation of fiducial markers can damage tissues, and lead to infections, since typically such markers remain within the tissues or organ after therapy concludes. This is particularly troublesome when treating a sensitive area, such as the uterus, where tissue damage and infection can lead to considerable problems such as bleeding and infertility. Another problem with most fiducials is that placement is permanent given the practical challenge of removing them. Unfortunately post treatment such fiducials introduce artifacts that obscure critical patient anatomy on follow up diagnostic imaging such as CT and MRI scans. Another problem is that body cavities, such as the vagina/cervix, the rectum/bowel, mouth/esophagus and artificial cavities such as laproscopic incisions, are narrow and do not easily permit precision lateral reach of instruments needed for fiducial implantation, making the traditional approach to fiducial marker implantation slow, tedious, and potentially traumatic to intervening tissue. Additionally, there is the problem that surgical instruments and anatomical targets in separate parts of the body are generally tracked by separate coordinate systems, and hence remain separate in the way that they appear to the surgical computer or surgeon.

It would be desirable to have devices and methods for treating portions of the body or sensitive organs prone to movement (e.g., treatment of uterine fibroids) non-invasively by using stereotactic radiosurgery. While this is technically achievable with pre-existing tools and systems, it is not efficient. For example, devices for affixing fiducial markers to the interior portion of the uterus or within its walls permit placement of only one marker at a time, and no means for easily finding and extracting these markers after use. There are safely and easily placed and removed intrauterine devices, for example for birth control purposes, but these are not designed to remain unmoving within a fibroid-laden uterus, and do not include the radiopaque materials, geometry, or spatial location of such portions required for radiological detection and tracking in a surgical or radiosurgical environment. It would also be desirable to be able to deploy a spatially separated array of fiducial markers by accessing a single point on or within patient anatomy. Finally, it would be desirable to have improved means of merging multiple coordinate systems while performing computer-guided surgery or related procedures. Thus, there is a need for improved devices and methods that allow for treating uterine fibroids non-invasively by using stereotactic radiosurgery in a manner that is safe, efficient, and effective.

BRIEF SUMMARY OF THE INVENTION

The present invention provides a removable marker implant having a multiple fiducial markers for delivery into a portion of the body (e.g., organ, body cavity, etc.) to provide improved and more accurate localization and tracking of the portion of the body, yet still allow for ready removal of the implant after therapy is complete. As described herein, fiducial markers are objects for which their position can be firmly ascertained by a detection modality, including but not limited to one or more of: X-ray or CT systems, MRI, ultrasound, sonography, and radiofrequency detection. The fiducial markers described herein can utilize any material suitable for detection by a given detection modality. "Radio-opaque" refers to a property of materials typically used for fiducial markers in the context of X-ray imaging including CT; materials that provide "MRI-enhancing" or "regions of MRI signal dropout" might be used in the context of MRI; materials that allow detection of "hyperechoic foci" and "acoustic shadows" may be used in the context of sonography; and materials that allow detection of the origin of RF signal emanation to instruments that enable detection of RF (e.g., Calypso) or other electromagnetic signals and triangulate in order to localize. It is appreciated that a combination of these materials to allow use of multiple detection modalities can be used as well.

In some embodiments, the marker implant is configured to distribute fiducial markers by extending or splaying multiple elongate members laterally outward to place multiple markers along surrounding tissues, while avoiding permanent implantation of fiducial markes within the tissue. In some embodiments, the implants avoids penetration and trauma to the tissues entirely. In some embodiments, the marker are disposed on semi-rigid elongate members that are coupled to a common base such that the movement of the entire implant observed under visualization is more representative of the position and movement of the organ or body cavity. In some embodiments, the implant is formed as a unitary component. Generally, the fiducial array relies on a fixed relationship (an anchorage) with respect to the relevant patient anatomy and at the same time form a substantially rigid construct. Yet still the device should be flexible enough to be both inserted and extracted, for example through a cannula.

In one aspect, the removable marker implant is configured for placement within the uterus for treatment of uterine fibroids. Along these lines, the implant can be configured with features suitable for use in an intrauterine device ("IUD"). Conventionally, IUDs are a general class of devices that carry out a function within the uterus, typically contraception. While such devices remain within the uterus sufficiently for contraception purposes or other functions, such implants are not stable enough for use as fiducial markers for stereotactic radiosurgery, which requires precise delivery of radiation to a target area. It is paramount that localization and tracking of the target is accurate, particularly in a sensitive region such as the uterus. Therefore, in contrast to conventional devices, the invention provides features that facilitate secure engagement of the implant along the walls of the uterus and a particular arrangement of discrete fiducial markers along portions of the implant to provide a suitable 3D visualization of the uterus during radiosurgery. Along these lines, in some embodiments, the implant includes at least three fiducial markers must be placed within the uterus in fixed locations such that the position of the uterus may be tracked during radiation delivery, ensuring that the radiation is sent to the correct location. Accordingly, the present invention includes an instrument for trans-vaginal/transcervical/intrauterine fiducial application. In one embodiment, the applicator pushes two or three fiducial markers with retention barbs into placement in the endothelial and myometrium wall, and to extract these after use. Radiosurgical planning and treatment delivery are then initiated.

While the devices and methods described herein are primarily described within the context of treating uterine fibroids, it is appreciated that the removable marker devices can be utilized in any portion of the body (e.g., organ, body cavity) where localization and/or tracking is desired for application of a therapy. Along these lines, the implants can be dimensioned, sized, or modified according to a particular application (number and arrangement of fiducial markers, size, shape and length of elongate elements and implant sheath, etc.). Examples of other portions of the body where such removable fiducial marker devices may be used include, but are not limited to: the gastrointestinal system including mouth, pharynx, esophagus, stomach, intestine, rectum, anus, and stomach, the renal system including kidney, ureter, bladder, urethra, within body cavities including the peritoneal cavity, the retroperitoneal space and the thoracic cavity, large and small intestine, bladder and ureter.

DETAILED DESCRIPTION OF THE INVENTION

Figure 1:
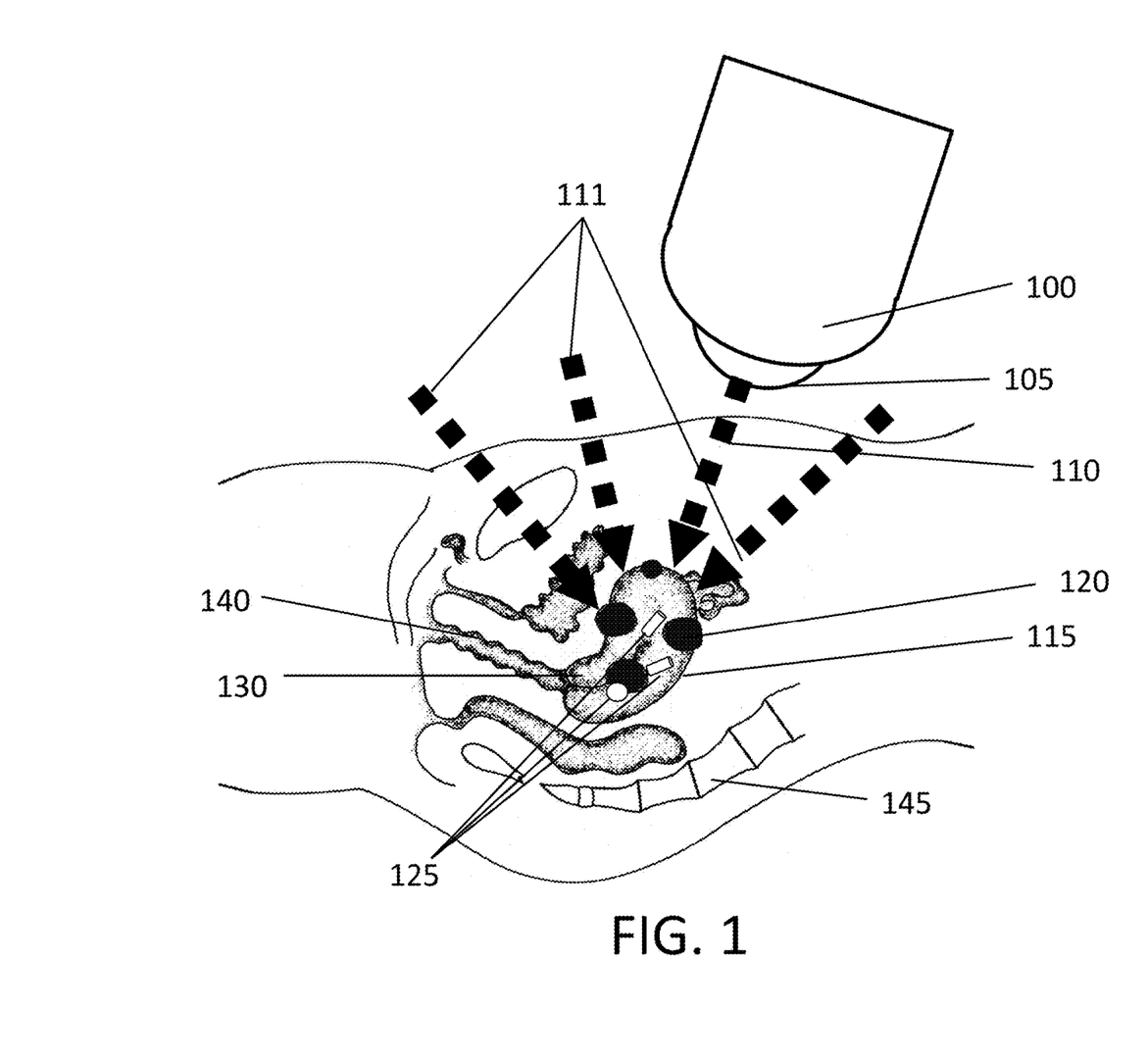
FIG. 1 illustrates the overall paradigm of the present invention, with a radiosurgical radiation source directing beams at an area defined by fiducial markers implanted within a leiomyomatous uterus.

FIG. 1 illustrates an overview of the present invention, including a radiosurgical radiation source directing beams at an area defined by fiducial markers that are held firmly in place within a leiomyomatous uterus such that movement of the uterus is accompanied by a commensurate movement of the fiducial markers. Radiologically-visible fiducial markers 125 have been placed within leiomyomatous uterus 115, which is designated as the radiosurgical target. The target may also be any other region with a fixed spatial relationship with respect to fiducial markers 125, for example individual fibroid 120. Fiducial markers have been placed via vagina 140 and cervix 130. Sacrum 145 is shown for reference. Linear accelerator head 100 directs ionizing radiation beam 110 outward in a precise intended direction and spatial pattern by passing through collimator 105, aimed at the radiosurgical target in uterus 115. As per standard radiosurgical technique, additional radiation beam trajectories 111 are aimed at the same radiosurgical target in order to maximize dose at the target and minimized it in areas peripheral to the target.

Figure 2:
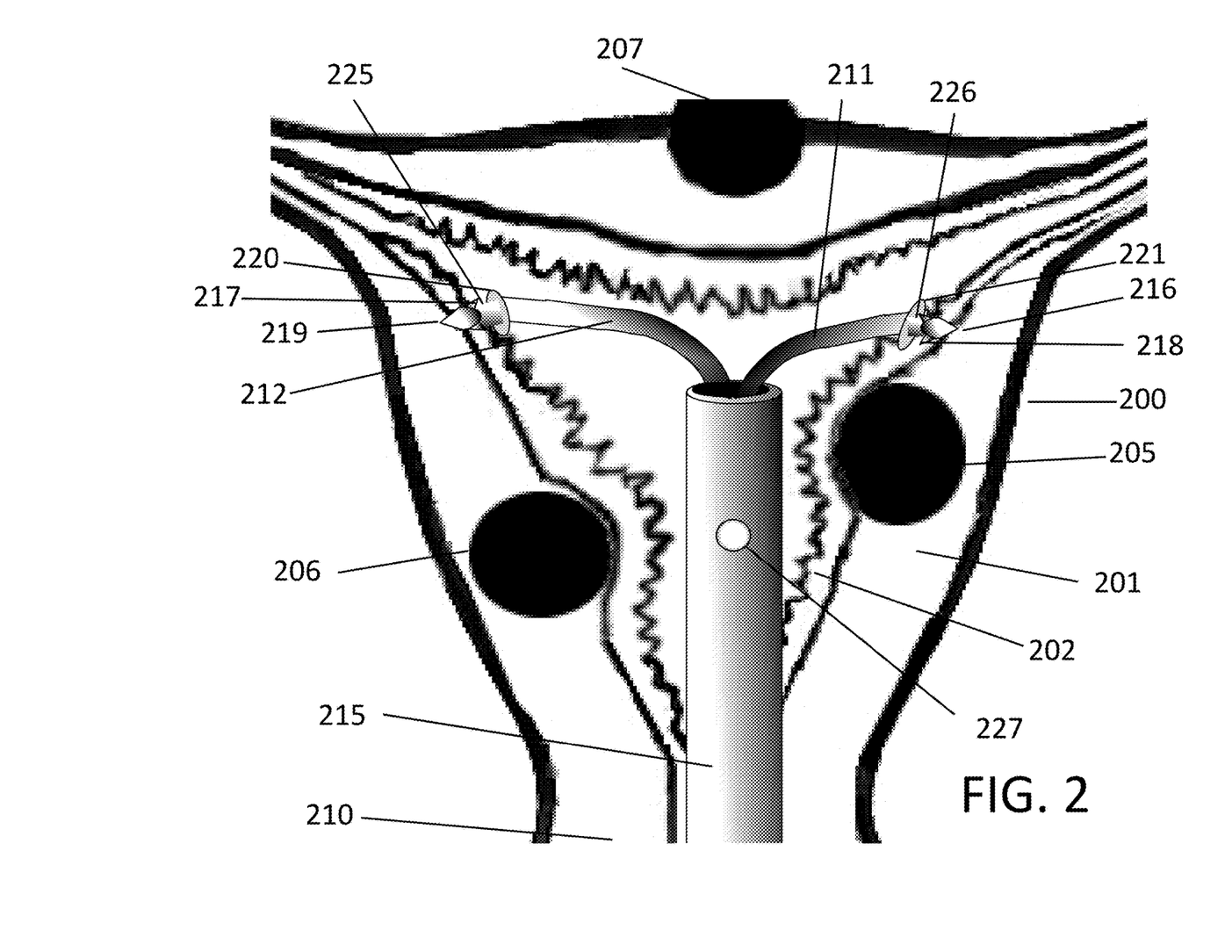
FIG. 2 illustrates one embodiment of the present invention comprising an intrauterine device that contains fiducial markers and endometrium-penetrating retention means.

FIG. 2 illustrates an exemplary intrauterine device that contains fiducial markers and endometrium-penetrating retention means. The device includes an elongated sheath (e.g., a shell, cannula, and the like) through which one or more fiducial markers are delivered into surrounding tissues, this elongated sheath thus constituting a point of origin for lateral deployment of the fiducial markers. As shown, sheath 215 is placed into uterus 200 via cervix 210, the elongate shape of the sheath serving to setting a point of origin for deployment. Uterus 200 contains fibroids (leiomyomas) 205, 206 and 207, and includes myometrium 201, endometrium 202 and cervix 210. Extensible arms 211 and 212 bring fiducial markers 225 and 226 into endometrium 202, penetrating that tissue via points 216 and 219. Penetration of points 216 and 219 is limited by penetration stoppers 225 and 226. Fiducial markers 225 and 226 are held into position in endometrium 202 by barbs 217 and 218 located behind points 216 and 219. Delivery sheath 215 includes fiducial marker 227 located on sheath 215 remains within uterus 200 during the subsequent radiosurgical treatment, providing a third dimension of spatial definition in addition to fiducial markers 225 and 226.

Figures 3A, 3B, 3C:
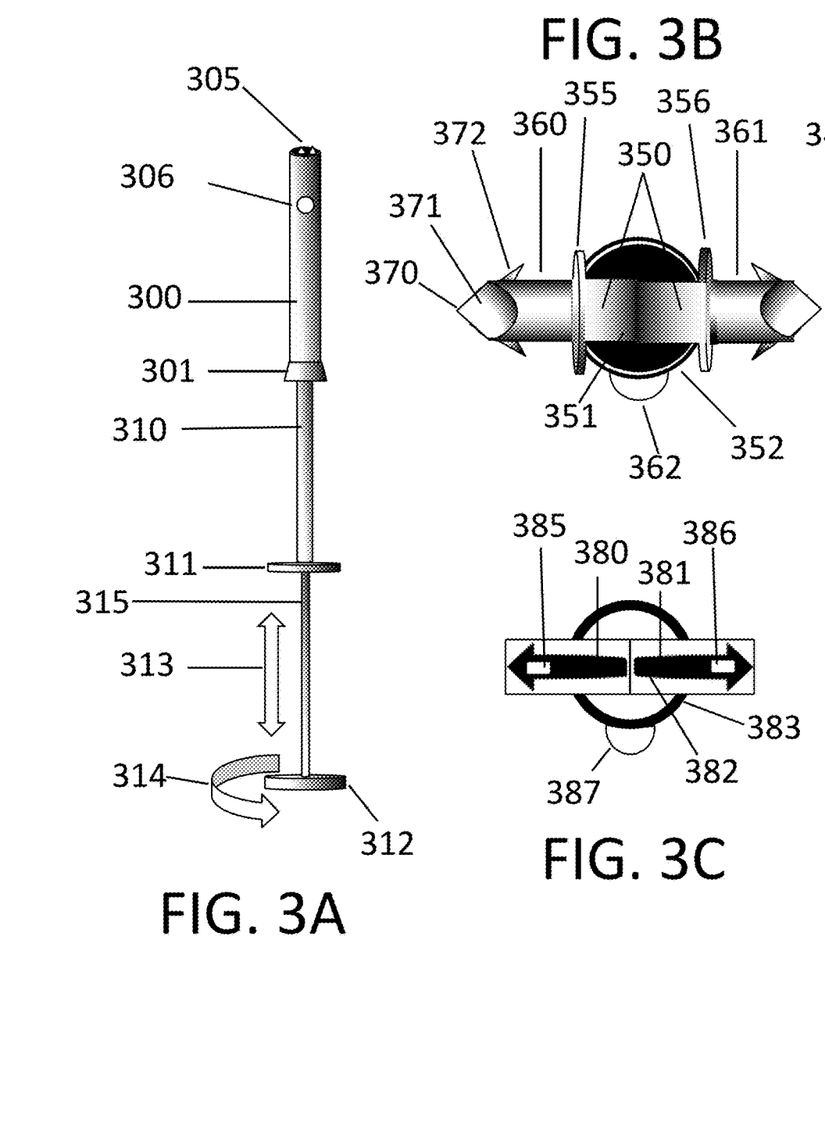
FIGS. 3A-3D detail one embodiment of the intrauterine fiducial marker array device engaged with the implantation applicator device, and the manner in which it is placed in retracted and extended positions.

FIGS. 3A, 3B and 3C detail an exemplary intrauterine fiducial marker array device engaged with the implantation applicator device, and the manner in which it is placed in retracted and extended positions. FIG. 3A illustrates the device in which the extensible arms and fiducial markers are retracted into sheath 300, which establishes a selectable point of origin for fiducial marker deployment. Sheath 300 has a proximal portion consisting of flange 301, which facilitates the introduction of engagement shaft 310 as described further below. Points 305 are seeing protruding from sheath 300, which includes shelf fiducial marker 306. Finger flange 311 serves as an anchor point for the clinician's fingers while the thumb presses thumb flange 312 in order to extend arm extension/retraction shaft 315 along direction 313. In some embodiments, by rotating 314 thumb flange 312, sheath 300 may be engaged or disengaged.

FIG. 3B illustrates an end-on view of sheath 352 as extensible arms 350 begin to be pushed out from and lateral to their former position within sheath 351. Point 370 and barb 372 are thereby pushed into adjacent soft tissue (for example endometrium) until their forward movement is stopped by penetration stopper 355 and 356. On each extensible arm and behind point 370 of barb 371 are extensible fiducial markers 360 and 361, which together with sheath-mounted fiducial marker 362, create a clear spatial reference to imaging or detection means as previously described.

FIG. 3C illustrates the direction of the extensible arm motion 380 and 381 with respect to sheath 383 in an end-on view of said sheath. Fiducial markers 385 and 386 are thus moved up and outward from the distal end of sheath 383 on extensible arms 382. In conjunction with sheath-mounted fiducial marker 387, a 3-dimensional tracking set is established on imaging or other spatial detection methods.

Figure 3D:
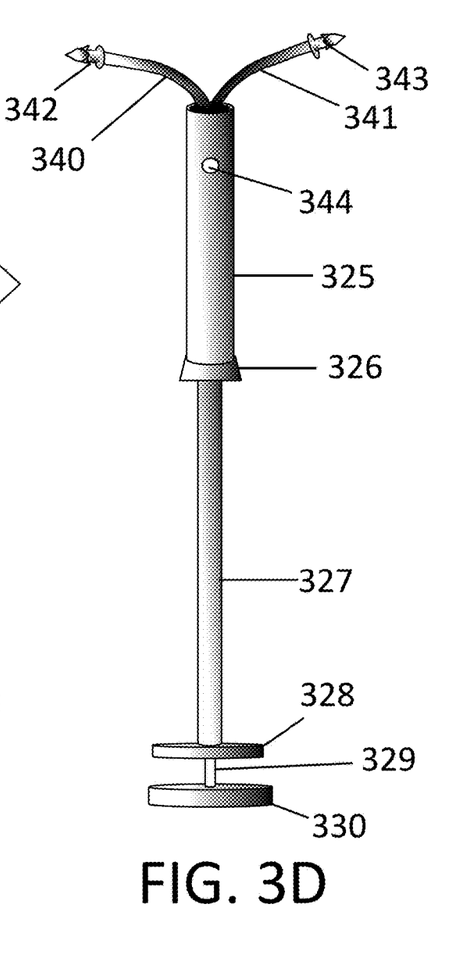

FIG. 3D illustrates an embodiment similar to that shown in FIG. 3A, except that in this figure, extensible arms 340 and 341 are in their extended positions. Extensible arm 340 includes point barb and fiducial marker 342, while extensible arm 341 includes point barb and fiducial marker 343. Sheath mounted fiducial marker 344 provides the third coordinate on imaging or other spatial detection methods for 3-D tracking. Sheath 325 has proximal flange 326 in order to facilitate the linear engagement with sheath engagement shaft 327. Finger flange 328 serves as an anchor point for the clinician's fingers while their thumb presses thumb flange 312 in order to extend arm extension/retraction shaft 329. In some embodiments, by rotating thumb flange 330, sheath 325 attached to arms 340 and 341 may be engaged or disengaged from sheath engagement shaft 327.

Figure 4:
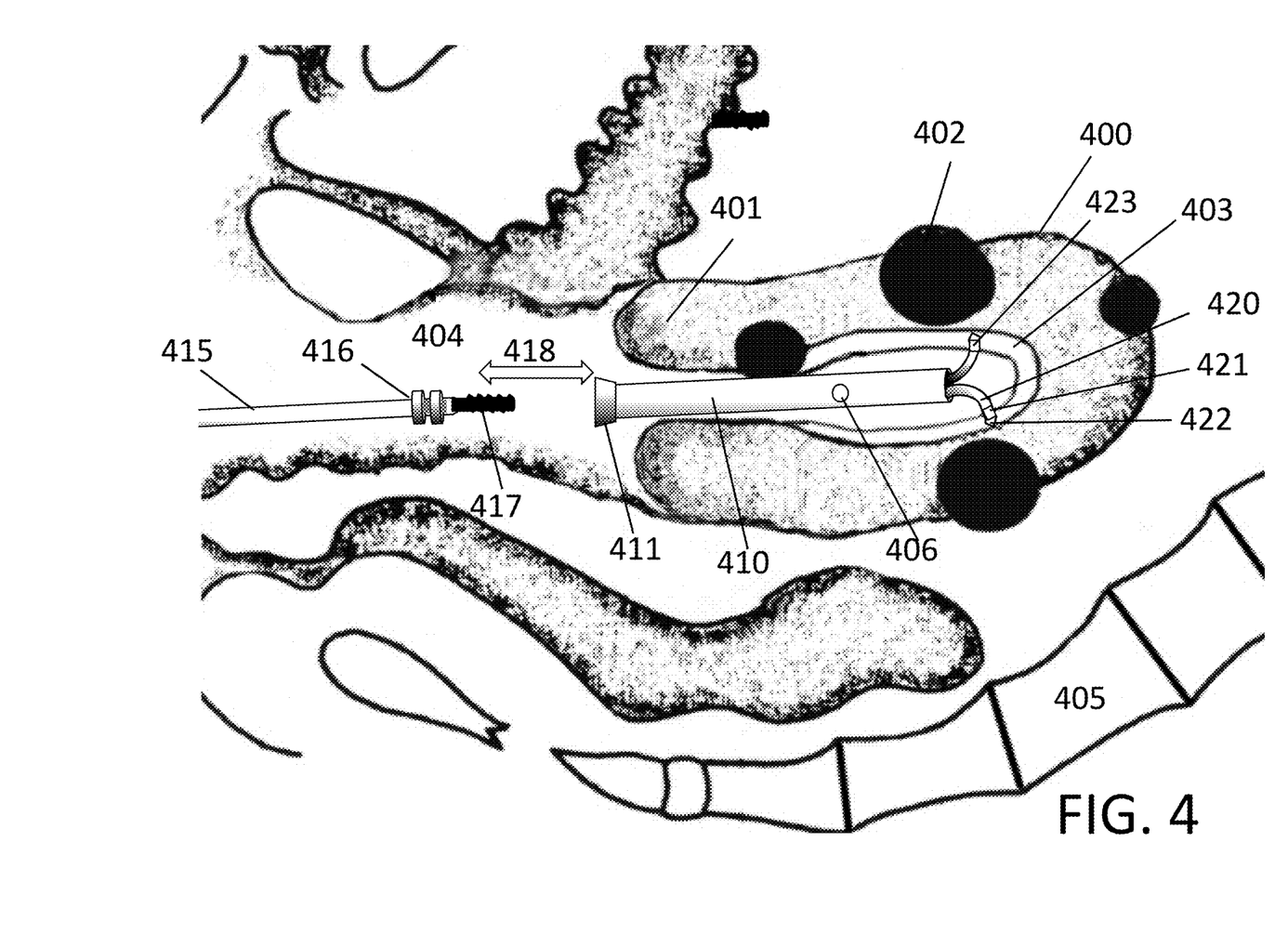
FIG. 4 illustrates one embodiment of the intrauterine fiducial marker array device as it detaches and re-attaches to the applicator device.

FIG. 4 illustrates another exemplary intrauterine fiducial marker array device as it detaches and re-attaches to the applicator device while within the uterus 400, which is lined by endometrium 403. Sacrum 405 is shown for anatomical reference. Sheath 410 is passed by the clinician through cervix 401 into uterus 400, which includes leiomyoma (fibroid) 402. Sheath 410 is shown passing through vagina 404 and cervix 401 into uterus 400, and establishes a selectable point of origin for fiducial marker deployment. Sheath 410 includes flange 411, this latter portion remaining outside cervix 401, with sheath fiducial 406 within the uterus 400. Arm extension shaft 415 includes linearly-extending engagement means 416 (e.g., protrusions, ridges, flanges, threads) and rotational engagement means 417, which engages with sheath 410 by movement 418 of IUD engagement shaft into or out of flange 411 and sheath 410, locking in place with internal recessions or threads that mate with rotational engagement means 417. Arm 420 includes fiducial marker 421, capped with point 422, designed to penetrate lodge in endometrium 403 in a spatially stable manner. Arm 423 is of the same or similar construction as arm 420.

Figure 5:
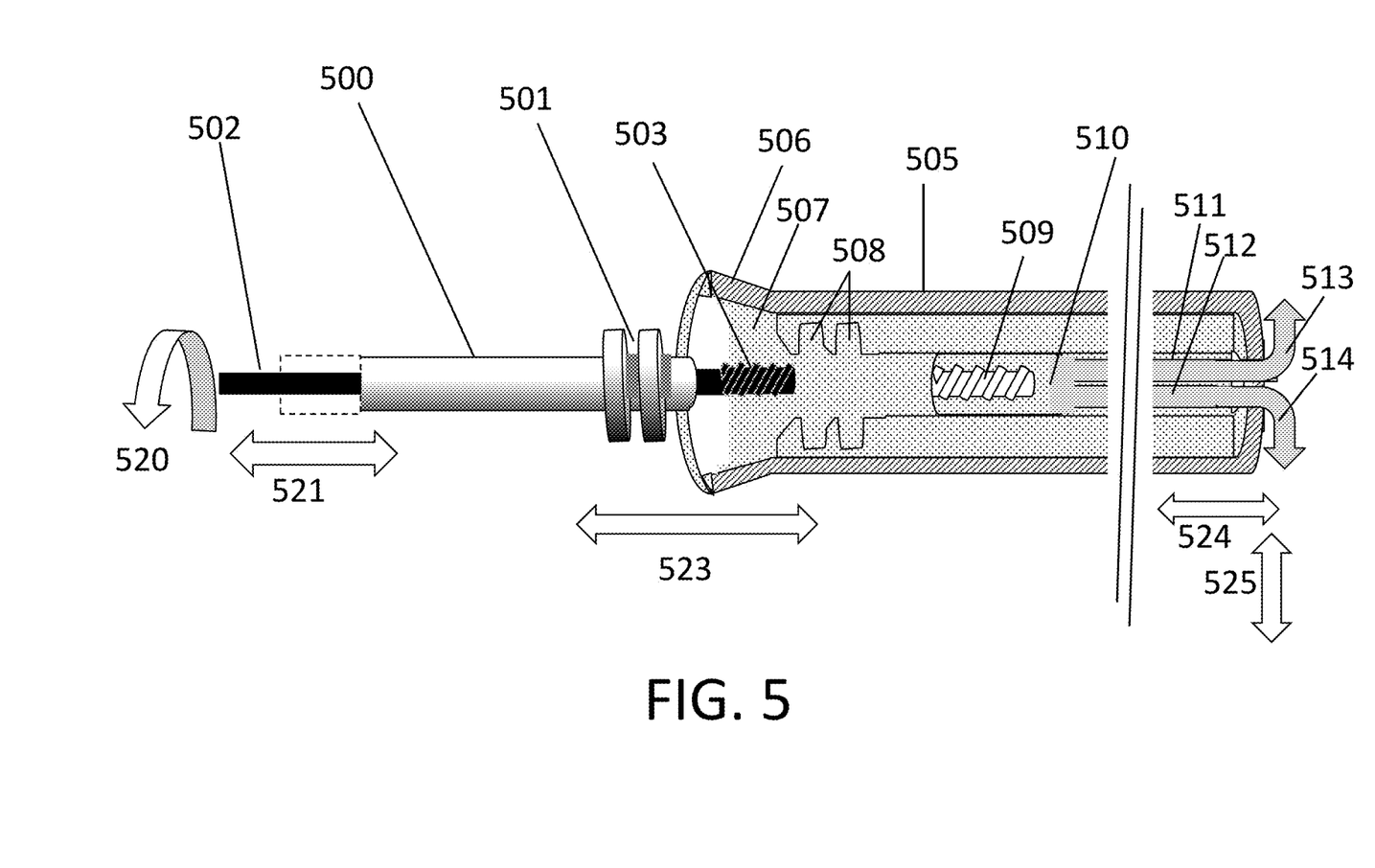
FIG. 5 details one embodiment of the intrauterine fiducial marker array device as it engages and dis-engages from the applicator device.

FIG. 5 details another exemplary intrauterine device as it engages and dis-engages from the applicator device. Applicator device includes a sheath engagement shaft 500 with an engagement rod 502 extending therethrough. Engagement shaft 500 of applicator device is designed for both linear movement 521 and rotational movement 520. Linear extension engagement movement 523 of engagement shaft into or out of lumen 507 of flange 506 of IUD sheath 505 mates male engagement means 501 with female engagement means 508 via linear movement 521. Rotational engagement means 503 mates with female rotational engagement means 509 via rotational movement 520 of engagement rod 502. Linear movement 521 of shaft 500 or rod 502 that are previously engaged with linear engagement means 508 or rotational engagement means 509 causes the forward movement of arm-base 510 and thus movement of arms 511, 512 in a forward direction 524, out from sheath 505, and distal arm portions 513 and 514 splay in an outward direction 525 due to the flexible shape memory of the material of which arms 511 and 512 are constructed. In some embodiments, the arms are constructed from polymers like polypropylene or polyethylene. In other embodiments, arms comprise a shape memory alloy.

Figure 6A:
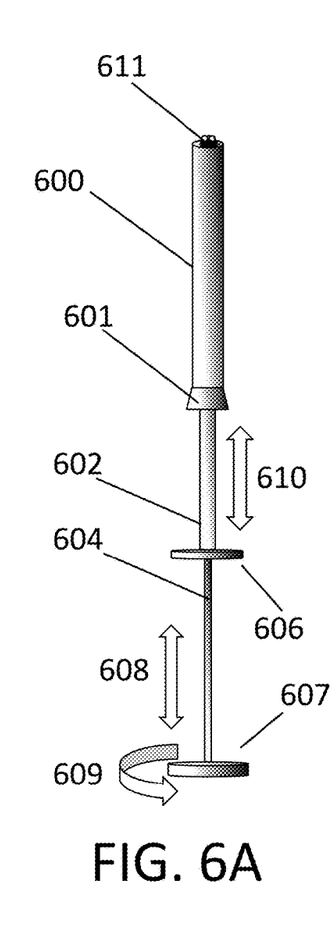
FIGS. 6A-6D illustrate a second embodiment of the present invention in which the intrauterine device contains fiducial markers without endometrium-penetrating retention means, and the manner in which it is placed in retracted and extended positions.

FIGS. 6A, 6B, 6C and 6D illustrate another exemplary intrauterine fiducial marker array device contains non-penetrating fiducial markers and the manner in which the device is placed. Similar to previous embodiments, the device includes markers on arms having retracted and extended positions. This embodiment lacks the endometrium-penetrating retention means shown in previous embodiments. FIG. 6A shows IUD sheath 600 with proximal flared portion flange 601. Sheath 600 removably attaches and locks to sheath engagement shaft 602, through which advancement of arm extension rod 604 deploys the fiducial markers 611. Extension rod 604 is configured for manual actuation, for example, with finger tab 606 and thumb tab 607 that are squeezed together by the user's hand, thus producing the longitudinally extending motion 608 of arm extension rod 604. In some embodiments, rotational motion 609 of engagement of arm extension shaft may be used to engage a base of the extension arms (similar to arm base 510 in FIG. 5, but not shown in this figure since it is inside sheath 600.) Longitudinally extending motion 610 of IUD engagement shaft pushes forward the non-penetrating fiducial markers 611 which are on carried on extensible and retractable arms, which in this figure are disposed within the sheath 600.

Figures 6B, 6C, 6D:
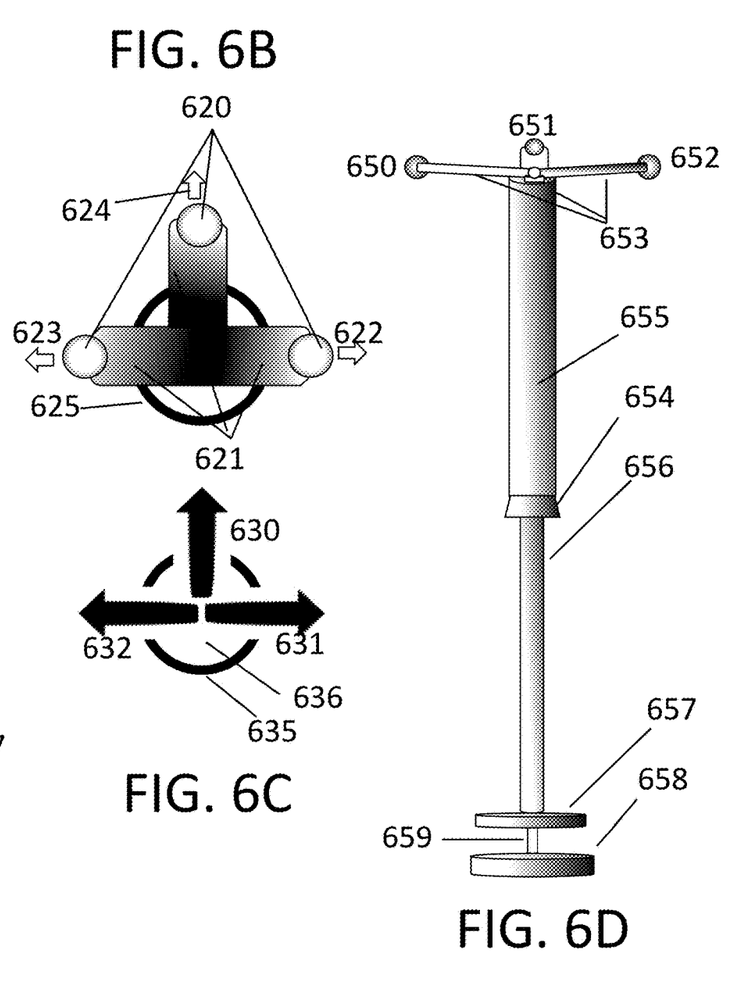

FIG. 6B shows non-penetrating fiducial markers 620 at distal ends of arms 621 emerging from a distal opening at the distal end of sheath 625. In this embodiment, the arms extend upward and splay outward along directions 622, 623, 624 for engagement against the uterine walls. This arrangement of arms allows the IUD marker device to engage against the uterine walls and secure the IUD in place.

FIG. 6C illustrates the direction that the extensible arms extend from a point of origin that has been set by the placement of the sheath or shell. Upon deployment, the arms extend forward and splay outward along directions 630, 631 and 632, emerging from the lumen 636 of the distal end of sheath 635. Including at least there fiducial markers establishes a 3-dimensional tracking set for imaging or other spatial detection methods.

FIG. 6D shows an another IUD marker device substantially similar to that shown in FIG. 6A, except that in this figure, extensible arms 653 are in their extended, deployed positions. Non-penetrating fiducial markers 650, 651 and 652 are attached along or near the distal ends of extension arms 653. In this embodiment, the distal ends are defined as blunt, atraumatic ends, for example, a bulbous or rounded shape ends, so as to prevent penetration or trauma to surrounding tissues. As shown, the arms 653 have unfolded outward from sheath 655 from its distal end. At the proximal end of sheath 655, is flange 654. Flange 654 improves the ease by which engagement shaft 656 may be inserted into linearly extending movable arm base of the arms 653. (The arm base is not shown in this figure as the base is disposed within the sheath). As in previous embodiments, pressure can be applied between finger tab 657 and thumb tab 658 in order to advance arm extension shaft 659 into the sheath and advance arm base to deploy the arms from the distal end of sheath into the expanded, deployed configuration shown.

Figure 7:
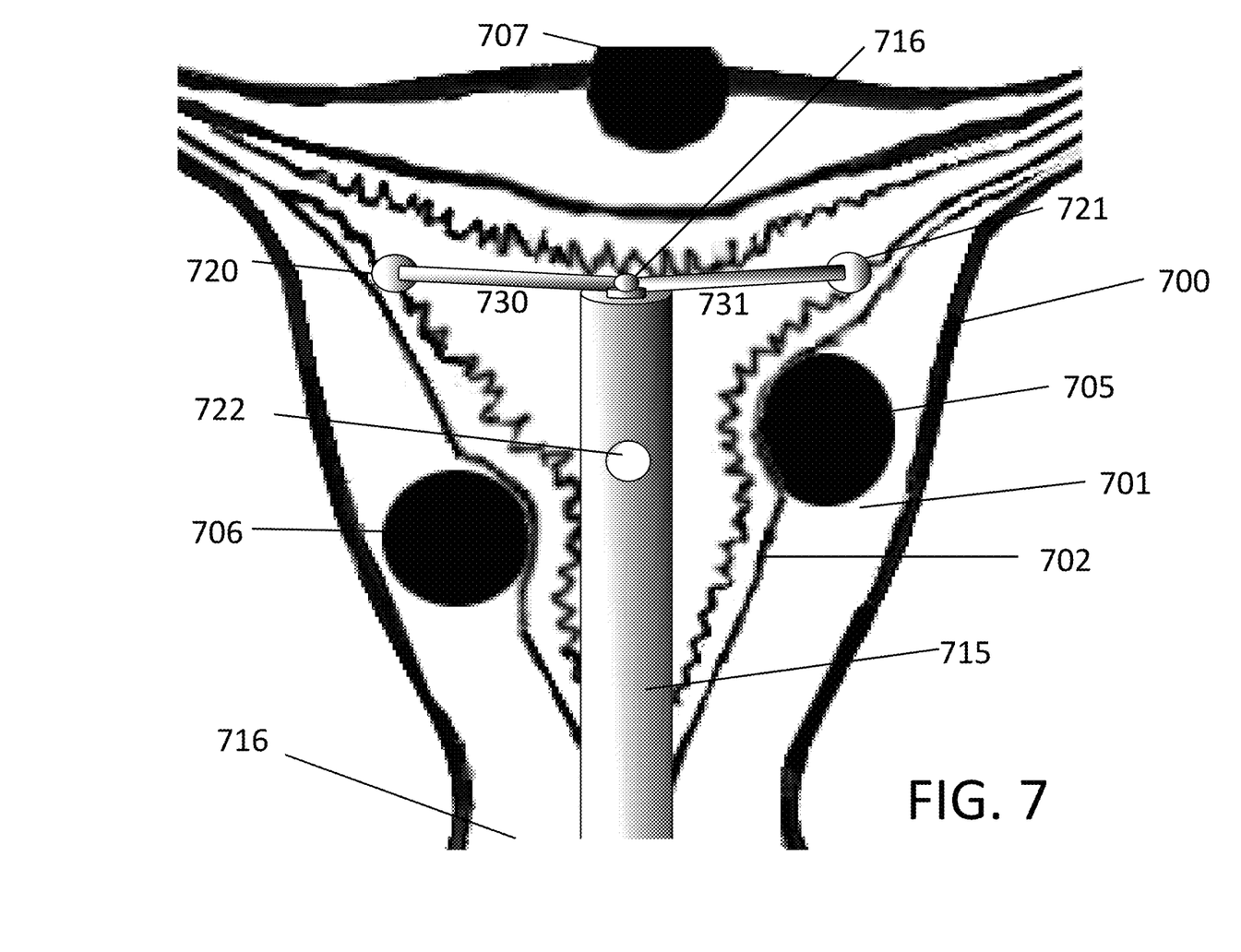
FIG. 7 illustrates a second embodiment of the present invention, without endometrium-penetrating retention means, in place within the uterus where the intrauterine device and its fiducial marker array is held in place in its extended form by the geometry of the uterus and cervix.

FIG. 7 illustrates another exemplary embodiment of a IUD marker device, without endometrium-penetrating retention means, deployed within the uterus. As shown, the fiducial marker array IUD device is held in place in its extended form by the geometry of the uterus 700 and cervix 716. Within uterus 700 is the normal muscular portion, myometrium 701, and the abnormal muscular portions, leiomyoma (fibroid) 705, 706 and 707. Sheath 715 with fiducial marker 722 is shown extending through cervix 715, into uterus 700, while extension arms 730 and 731 with fiducial markers 720 and 721 are fully extended so as to remain in place by virtue of the geometric constraints of the space with uterus 700. In some embodiments, the distal portions of the arms when in the expanded, deployed configuration are rigid or semi-rigid so as to lodge against the interior of the uterus and maintain anchored or secured within the uterus in a substantially fixed position suitable for tracking the location and movement of the uterus during the course of radiosurgery therapy. After therapy, arms 730 and 731 can be retracted into the sheath 715 until the sheath contains the arms 730, 731 and fiducial markers 720 and 721, after which the sheath can be freely moved out through cervix 716 and removed.

Figures 8A, 8B, 8C:
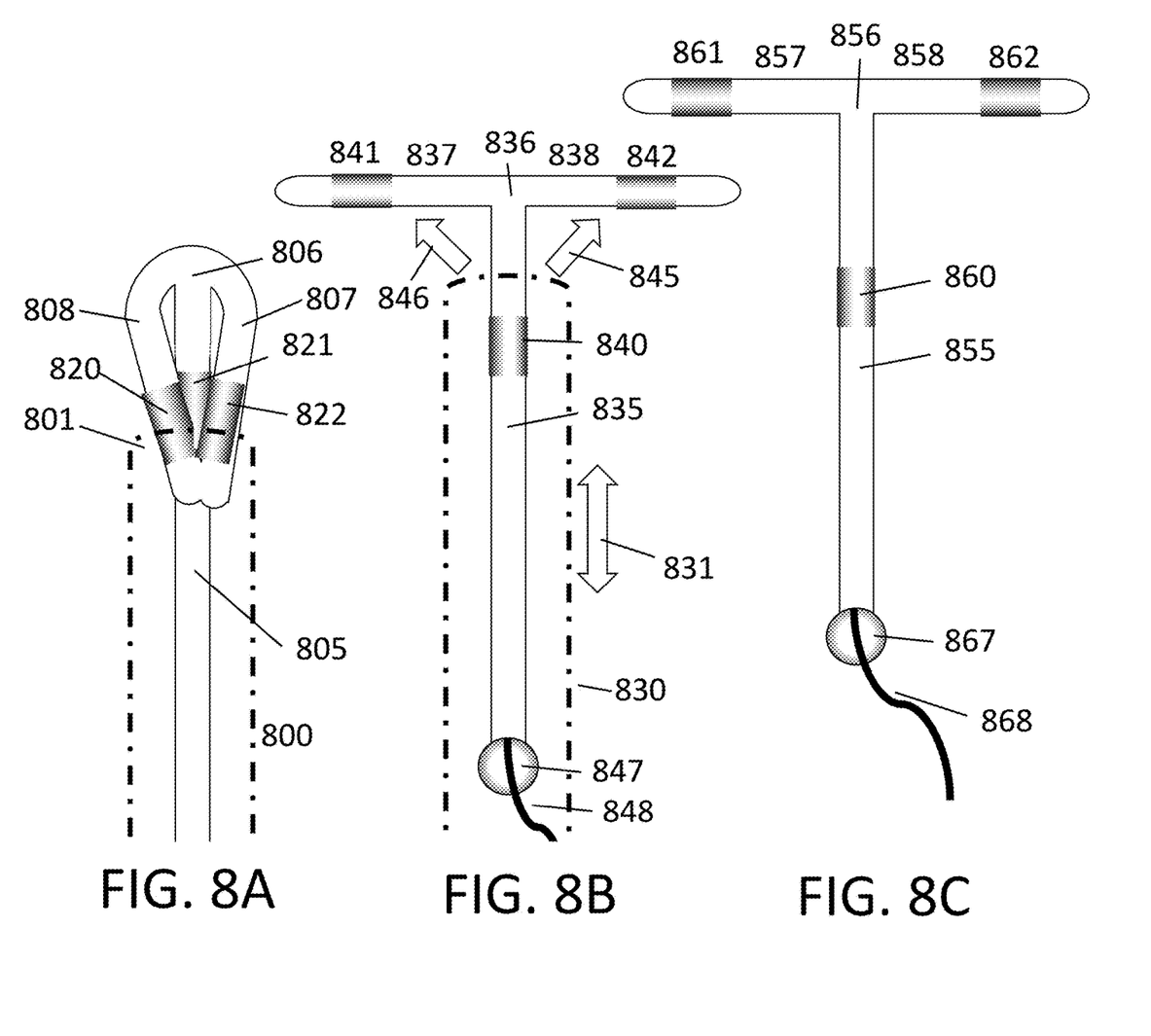
FIGS. 8A-8C illustrate a third embodiment of the present invention in which splaying movement of the fiducial marker-bearing arms is accomplished via the flexible, shape memory of the material.

FIGS. 8A, 8B and 8C illustrate a third embodiment of the present invention in which splaying movement of the fiducial marker-bearing arms is accomplished via the flexible, shape memory of the material. As illustrated, this embodiment has no endometrium-penetrating retention means, and is held in place in its extended form by the geometry of the uterus and cervix.

FIG. 8A shows yet another exemplary IUD marker device. The device includes base rod 805 and the tips of arms 807 and 808, along with fiducial markers 820 and 822 and base rod fiducial marker 821, are tucked within lumen 801 of sheath 800. In this embodiment, base rod 805 is integrally formed at the time of manufacture of a shape-memory material, for example polypropylene, with arms 807 and 808 forming a flexible "T"-shaped configuration due to deformation/re-formation particularly in the region of area 806 where the portions converge. However here in FIG. 8A, arms 807 and 808 are held constrained into a folded position against shaft 805 by the wall of sheath 800 on the outside of lip of lumen 801 due to their flexibility. In this compact folded configuration, the device may be inserted through the cervix into the uterus (not shown in this figure).

FIG. 8B shows the IUD marker device with arms 837 and 838 in the extended, deployed configuration after retraction of sheath 830 by resilient unfolding and extension of the arms splaying along direction 845. Arms 837 and 838 may be joined to base rod 835 at intersection 836 where each of these parts is integrally formed at the time of manufacture. In some embodiments, the IUD marker device can be formed from a shape-memory materials including polymers such as polyethylene or polypropylene. In the deployed configuration, fiducial markers 840, 841 and 842 are at a maximum distance from one another, which facilitates optimal spatial tracking methods. In this embodiment, base rod 835 has blunt atraumatic end 847 and extraction string 848.

FIG. 8C shows the IUD marker device in the deployed configuration with the sheath portion fully removed. In this deployed configuration, the IUD marker device rests in the uterus while the fiducial markers are tracked and radiation treatment is delivered. In some embodiments, base rod 855 is integrally formed at the time of manufacture and therefore joined via flexible junction portion 856 to arms 857 and 858. This flexible T-shaped structure may be composed of a shape memory material, including polymers such as polyethylene or polypropylene. Fiducial marker 860, 861 and 862 are disposed on each of base rod 855, arm 857 and arm 858. Base rod 855 has a blunt proximal end 867, and extraction string 868 which can be pulled on in order to retract the device from position in the uterus after therapy. During such a procedure, the flexible nature of arms 857 and 858, particularly where they converge at region 856 causes the arms to bend upward (away from base rod 855), and thereby form a more compact configuration while passing out from the cervix (not shown). Thus, in this embodiment, the IUD marker device can be removed without returning the arms into the sheath. In other embodiments, the sheath can be reinserted and the IUD marker device withdrawn into the sheath.

In another aspect, the invention pertains to methods of implanting temporarily a IUD marker device into a portion of a patient's body to facilitate locating and tracking of the portion of the body during a course of therapy, typically radio surgery. These methods are particularly advantageous for use in tracking a uterus in a radiosurgery treatment of fibroids. In a preferred embodiment, the method includes insertion of an IUD marker device by a clinician in a non-pregnant woman with uterine fibroids. A pelvic examination is done prior to insertion in order to determine the position of the uterus. Subsequently, the vagina is held open with a speculum, and a tenaculum is used to hold the cervix and uterus still. The distance to the back and sides of the available space within the uterine cavity may be determined via insertion of a sounding probe, thereby ascertaining that the present device can be safely inserted. The IUD marker device is then inserted while enclosed within the sheath or insertion tube, which is passed through the cervix, to the back of the uterus, and then forward again for approximately one centimeter prior to deploying the arms with their attached fiducial markers. Following execution of a radiosurgical plan to the fibroids, the IUD marker device may be removed. In some embodiments, removal may be achieved may by re-inserting the arm deployment rod and retracting the arms, then retracting the base of the device. Alternatively, a monofilament string may left protruding from the cervix into the vagina or to the external environment in order to facilitate removal. Radiosurgical treatment planning is accomplished using the fiducial markers to make clear the position of the uterus at the time of pre-operative imaging. Dose that would be received by the ovaries, fallopian tubes, bladder, bowel and other areas is closely monitored, and the trajectory of the planned radiation beams in any given treatment plan is adjusted accordingly. Radiosurgical treatment delivery is then initiated. Real-time (during the radiosurgical procedure) imaging is done throughout the radiosurgical treatment deliver, for example, by one or more kV (diagnostic-intensity) x-ray detectors, CT or MRI, using the fiducial markers to track the real-time position of the uterus, with the trajectory of radiation treatment beams adjusted accordingly.

In alternative embodiment, the fiducial array may be deployed near the site of a lesion within the colon in order to radiographically track movement of the lesion during radiosurgery. In the context of minimally-invasive laparoscopic surgeries, deploying fiducial markers at a selected location with the intestine could provide spatial context for both the endoscopic view, and for a laparoscopic view.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A device for placing one or more radiosurgical fiducial markers into a uterus, the device comprising:
    the one or more radiosurgical fiducial markers disposed on a distal portion of each of a plurality of elongate members; and
    a sheath in which the plurality of elongate members are at least partly disposed, wherein the plurality of elongate members are movable between a delivery configuration and a deployed configuration,
    wherein in the delivery configuration, the plurality of elongate members are substantially contained within the sheath,
    wherein in the deployed configuration, the distal portions of each of the plurality of elongate members having the one or more radiosurgical fiducial markers extend through one or more openings in the sheath for placement along the uterus to facilitate 3D visualization and/or tracking of the uterus,
    wherein the one or more radiosurgical fiducial markers are fixed relative to each other in the deployed configuration, and
    wherein the plurality of elongate members comprise a rigid material thereby fixing the one or more radiosurgical fiducial markers relative to each other in the deployed configuration.

2. The device of claim 1, wherein the sheath comprises at least one of the one or more radiosurgical fiducial markers and each of the plurality of elongate members comprises at least one of the one or more radiosurgical fiducial markers at or near a distal of each of the plurality of elongate members, whereby, when in the deployed configuration, 3-dimensional spatial positions of the one or more radiosurgical fiducial markers facilitate tracking of the uterus by visualization techniques.

3. The device of claim 1, wherein the plurality of elongate members comprises a pair of elongate members or three elongate members.

4. The device of claim 1, wherein the plurality of elongate members are slidably disposed within a lumen of the sheath and movable between the delivery and deployed configurations by sliding within the lumen.

5. The device of claim 4, wherein each of the plurality of elongate members comprises a distal barb for penetrating engagement with a tissue of the uterus when deployed.

6. The device of claim 4, wherein each of the plurality of elongate members comprises a distal atraumatic tip to engage a tissue of the uterus without penetration.

7. The device of claim 4, wherein the plurality of elongate members are proximally coupled to a base that is slidable through the lumen in the sheath.

8. The device of claim 7, further comprising:
an applicator that is releasably attachable to the base for distal advancement of the base within the lumen to deploy the plurality of elongate members.

9. The device of claim 1, further comprising:
an applicator that is releasably attachable to the sheath to facilitate deployment and retraction of the plurality of elongate members and removal of the sheath after therapy.

10. The device of claim 9, wherein the applicator comprises an engagement shaft that releasably engages with the sheath by mating corresponding coupling features.

11. The device of claim 10, wherein the applicator further comprises a rod advanceable through the engagement shaft that releasably engages with a base of the plurality of elongate members by mating the corresponding coupling features.

12. The device of claim 11, wherein the corresponding coupling features comprise a male feature selected from the group consisting of: one or more protrusions, ridges, flanges and threads and a female feature selected from the group consisting of: one or more recesses and internal threads.

13. The device of claim 11, wherein the engagement shaft comprises a finger tab at a proximal end of the engagement shaft and the rod comprises a thumb flange at a proximal end of the rod, to facilitate manual manipulation of the engagement shaft relative the rod.

14. The device of claim 9, wherein the applicator is releasably attachable to the sheath via linear engagement means or rotational engagement means.

15. The device of claim 1, wherein the plurality of elongate members are configured such that, in the deployed configuration, the plurality of elongate members splay laterally outwards in a distributed array.

16. The device of claim 15, wherein the plurality of elongate members are formed of a shape memory material.

17. The device of claim 15, wherein the plurality of elongate members are formed, at least in part, of a flexible material.

18. The device of claim 1, wherein the sheath is dimensioned and configured for placement of a distal portion of the sheath within the uterus by insertion through a cervix.

19. The device of claim 18, wherein the sheath comprises a proximal flange dimensioned to engage tissues and prevent insertion beyond the cervix.

20. The device of claim 1, wherein the one or more radiosurgical fiducial markers and the sheath are sufficiently rigid and sized such that, in the deployed configuration, the one or more radiosurgical fiducial markers and the sheath remain in a substantially fixed position within the uterus to facilitate tracking the uterus during radiosurgery therapy.

21. A removable marker implant device for inserting one or more radiosurgical fiducial markers into a uterus, the implant device comprising:
a removable implant having a plurality of elongate members extending laterally outward from a central rod; and
the one or more radiosurgical fiducial markers disposed on a distal portion of each of the plurality of elongate members of the implant device,
wherein the plurality of elongate member are flexible so as to be movable between a constrained delivery configuration and a deployed configuration, wherein:
in the delivery configuration, the plurality of elongate members are flexed towards the central rod by a sheath to facilitate delivery into the uterus, and
in the deployed configuration the plurality of elongate members extend and splay laterally outward to engage the uterus when released from the sheath,
wherein the one or more radiosurgical fiducial markers are fixed relative to each other in the deployed configuration, and
wherein the plurality of elongate members comprise a rigid material thereby fixing the one or more radiosurgical fiducial markers relative to each other in the deployed configuration.

22. The implant device of claim 21, wherein the plurality of elongate members and the central rod are formed as a unitary component.

23. The implant device of claim 21, wherein the plurality of elongate members and the central rod are formed of a shape memory material.

24. The implant device of claim 21, wherein each of the plurality of elongate members have distal atraumatic tips and the implant device is configured for delivery and deployment in the uterus.

* * * * *

UNITED STATES PATENT AND TRADEMARK OFFICE
CERTIFICATE OF CORRECTION

| | |
|---|---|
| PATENT NO. | : 11,684,446 B2 |
| APPLICATION NO. | : 16/787234 |
| DATED | : June 27, 2023 |
| INVENTOR(S) | : John R. Adler, Jr. and M. Bret Schneider |

It is certified that error appears in the above-identified patent and that said Letters Patent is hereby corrected as shown below:

In the Claims

Column 10 Line 63, Claim 2: please delete "near a distal of each" and insert --near a distal end of each--.

Signed and Sealed this
Twenty-second Day of August, 2023

Katherine Kelly Vidal
*Director of the United States Patent and Trademark Office*